United States Patent
Somasundaram et al.

(10) Patent No.: US 7,103,931 B2
(45) Date of Patent: Sep. 12, 2006

(54) TABLE DRIVE SYSTEM FOR MEDICAL IMAGING APPARATUS

(75) Inventors: Baskar Somasundaram, Bangalore (IN); Shaji Alakkat, Bangalore (IN)

(73) Assignee: General Electric Company, Schenectady, NY (US)

( * ) Notice: Subject to any disclaimer, the term of this patent is extended or adjusted under 35 U.S.C. 154(b) by 139 days.

(21) Appl. No.: 10/928,341

(22) Filed: Aug. 28, 2004

(65) Prior Publication Data

US 2006/0042009 A1    Mar. 2, 2006

(51) Int. Cl.
*A61B 6/04*   (2006.01)
*A61G 13/00*  (2006.01)

(52) U.S. Cl. ............... 5/601; 5/616; 378/209
(58) Field of Classification Search .......... 5/601, 5/616; 378/209; 108/143
See application file for complete search history.

(56) References Cited

U.S. PATENT DOCUMENTS

| | | | |
|---|---|---|---|
| 4,771,785 A * | 9/1988 | Duer | 600/415 |
| 4,912,754 A | 3/1990 | Steenburg et al. | |
| 4,984,774 A * | 1/1991 | Zupancic et al. | 5/601 |
| 5,048,071 A | 9/1991 | Steenburg et al. | |
| 5,156,166 A | 10/1992 | Sebring | |
| 5,572,569 A | 11/1996 | Benoit et al. | |
| 6,038,718 A | 3/2000 | Pennington et al. | |
| 6,240,582 B1 * | 6/2001 | Reinke | 5/601 |
| 6,353,949 B1 | 3/2002 | Falbo | |
| 6,615,428 B1 * | 9/2003 | Pattee | 5/601 |
| 6,857,147 B1 * | 2/2005 | Somasundaram | 5/601 |
| 6,986,179 B1 * | 1/2006 | Varadharajulu et al. | 5/611 |

FOREIGN PATENT DOCUMENTS

EP    0268555    10/1987

OTHER PUBLICATIONS

EMS Limited, Internet Website, Aug. 28, 2004.
Elegance Table, Aug. 28, 2004.
Stille Internet Website, Aug. 28, 2004.

* cited by examiner

*Primary Examiner*—Michael Trettel
(74) *Attorney, Agent, or Firm*—Michael G. Smith; Peter Vogel; Carl Horton

(57) ABSTRACT

A drive system for a patient support table in a medical imaging apparatus is provided. In some embodiments, the system comprises at least one first drive means for driving a patient support surface in at least one first direction, at least one second drive means for driving the patient support surface in at least one second direction, wherein the at least first drive means and the at least second drive means are mounted on at least one common mounting member.

20 Claims, 4 Drawing Sheets

US 7,103,931 B2

TABLE DRIVE SYSTEM FOR MEDICAL IMAGING APPARATUS

FIELD OF THE INVENTION

This invention relates generally to table drive systems, and more particularly, to a drive system for patient support table in diagnostic medical imaging apparatus such as, for example an X-ray apparatus, Magnetic Resonance Imaging device, vascular devices, etc.

BACKGROUND OF THE INVENTION

Typically, drive systems for a patient support table in a diagnostic medical imaging equipment include mechanisms for effecting longitudinal and lateral movement to a patient support surface for enabling convenient positioning of a patient for medical examination.

Known configurations of a drive system for patient support table include a longitudinal drive mechanism and a lateral drive mechanism having one of a manually operable configuration or a drive motor.

However, these known configurations do not provide for an optimum positioning and arrangement of the drive mechanisms, wherein the drive system (i) becomes significantly compact (ii) provides smooth motorized motion with low play and/or slip in the driveline and (iii) ensures easy access and increased safety to patients.

BRIEF DESCRIPTION OF THE INVENTION

The above-mentioned shortcomings, disadvantages and problems are addressed herein, which will be understood by reading and studying the following specification.

In an embodiment, a drive system for a patient support table is provided. The system comprises at least one first drive for driving a patient support surface in at least one first direction, at least one second drive for driving the patient support surface in at least one second direction, wherein the at least first drive and the at least second drive are mounted on at least one common mounting member.

In another embodiment, a drive system for a patient support table is provided. The system comprises at least one driving member in coordinating relationship with at least one driven member for moving a patient support surface, wherein the driving member is configured to move along with the patient support surface.

In yet another embodiment, a patient support table comprising at least one patient support surface is provided. The patient support surface is configured movable by at least one of a first drive and a second drive mounted on at least one common mounting member, at least one of said drives including at least one driving member and at least one driven member, wherein the driving member is configured movable along with the patient support surface.

Apparatus, systems, and methods of varying scope are described herein. In addition to the aspects and advantages described in this summary, further aspects and advantages will become apparent by reference to the drawings and by reading the detailed description that follows.

DETAILED DESCRIPTION OF THE INVENTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Various embodiments of this invention provide a drive system for patient support table in a diagnostic medical imaging apparatus such as, for example, an X-ray apparatus, Magnetic Resonance Imaging device, vascular device, etc. However the embodiments are not so limited, and may be implemented in connection with other systems such as, for example, gamma ray devices, nuclear devices, etc.

In various embodiments, a drive system for a patient support table is provided, wherein the drive system comprises at least one first drive for moving a patient support surface of the table in at least one first direction, and at least one second drive for moving the patient support surface in at least one second direction, wherein the at least first drive and the at least second drive are mounted on at least one common mounting member.

Figure 1:
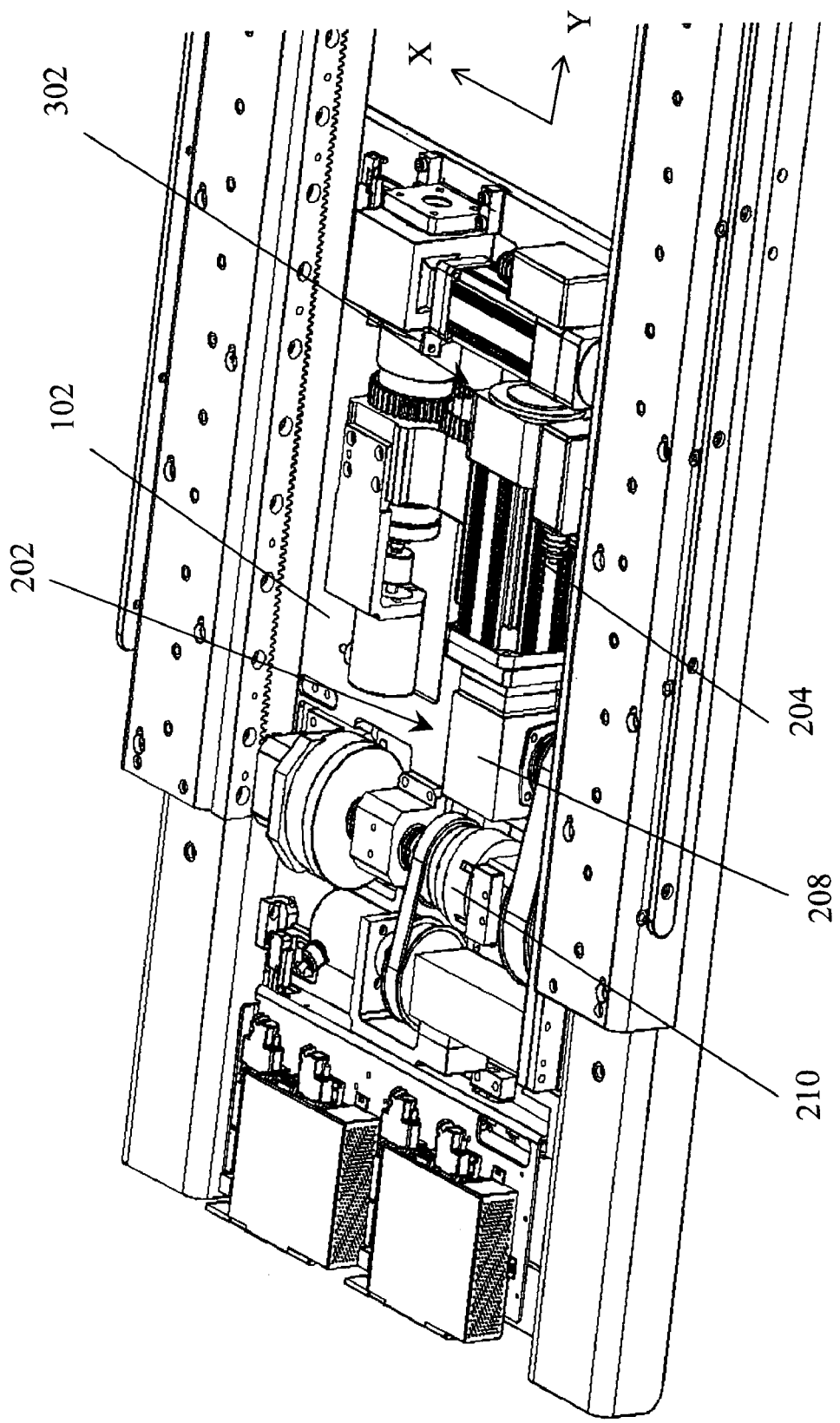
FIG. 1 shows a perspective view of a table drive system according to one embodiment of the present invention.

FIG. 1. shows an exploded view of a patient support table according to one embodiment of this invention, wherein the table comprises at least one patient support surface (not shown) for supporting a patient for examination. The patient support surface is rigidly coupled to a longitudinal plate 102 from the underside of the patient support surface. The longitudinal plate 102 and the patient support surface are movably supported over a tilt plate 104 (see FIG. 4) through a linear bearing 106 (see FIG. 4).

In an example, the linear bearing 106 may include a linear block 108 (see FIG. 3) mounted on to the tilt plate 104 and a guide member 110 mounted on to the longitudinal plate 102.

In the embodiment shown in FIG. 1, at least one first drive 202 is mounted on the longitudinal plate 102 (e.g. a mounting member) for moving the patient support surface along a first direction (Y) e.g. longitudinal direction of the patient support surface. The first drive 202 includes a drive motor 204 coupled to the patient support surface through a transmission comprising e.g. a gearbox 208 and a clutch 210.

In other embodiments, the first drive 202 may include at least one of a friction drive, hydraulic and pneumatic actuator for providing longitudinal motion to the patient support surface.

In the embodiment shown in FIG. 1, at least one second drive 302 is mounted on the longitudinal plate 102 (mounting member), for moving the patient support surface along a second direction (X) e.g. lateral direction to the patient support surface.

It should be noted that the first drive 202 and the second drive 302 are mounted in common over the longitudinal plate 102 (mounting member).

For example, the first drive 202 and the second drive 302 are mounted using a fixture such as, for example, a support bracket 313 (shown in FIG. 2) fastened or welded on to the longitudinal plate 102.

This common mounting arrangement makes the entire table drive system significantly compact by eliminating projection of the drive components along the lateral direction (X) of the table. As the system becomes compact, interference of user interface (UIF) cables with the second drive 302 is also avoided. Furthermore, improved access by user towards the patient support surface for patient positioning in the imaging area becomes possible.

Figure 2:
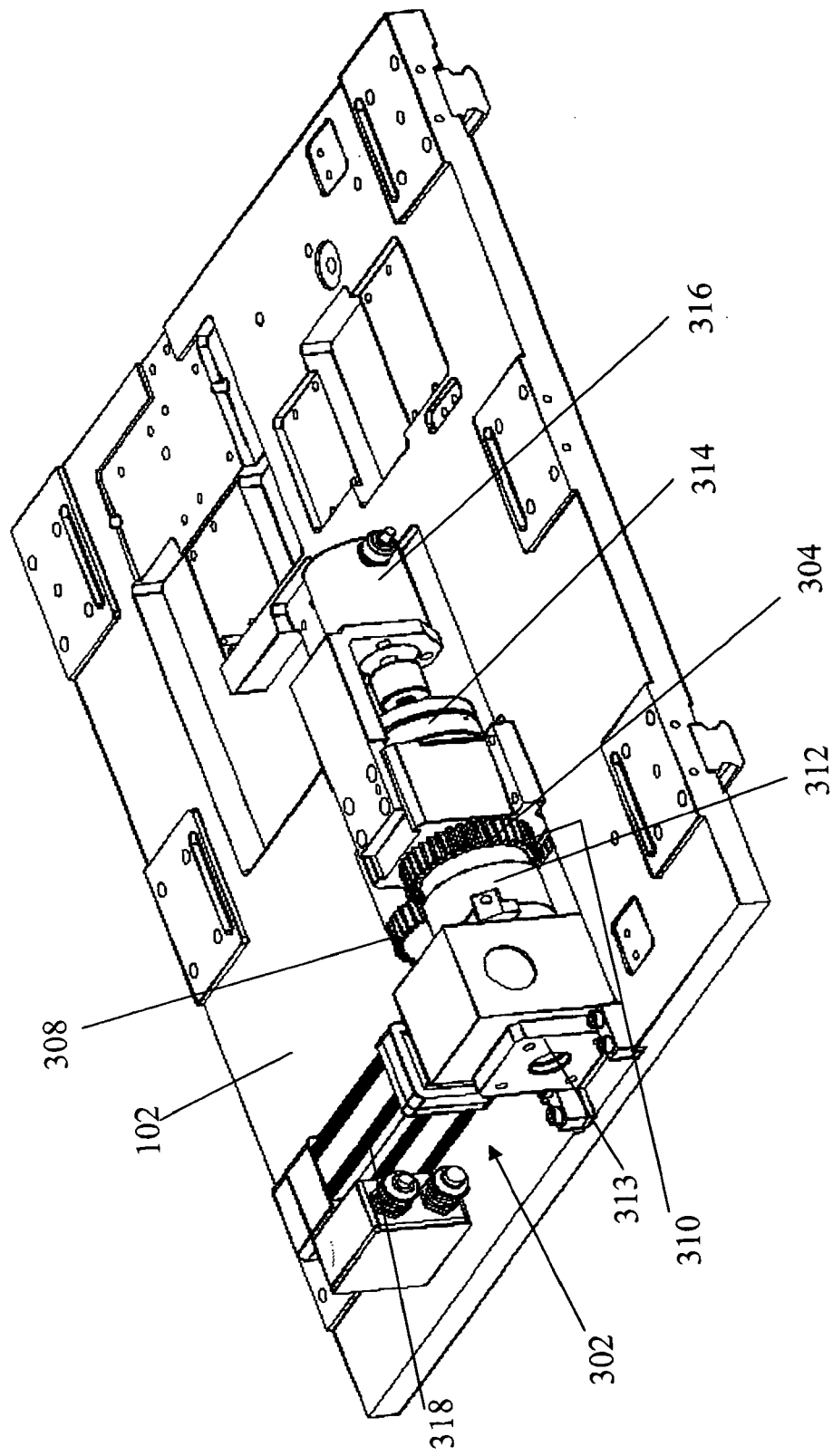
FIG. 2 shows an exploded perspective view of a table drive system of FIG. 1.
Figure 3:
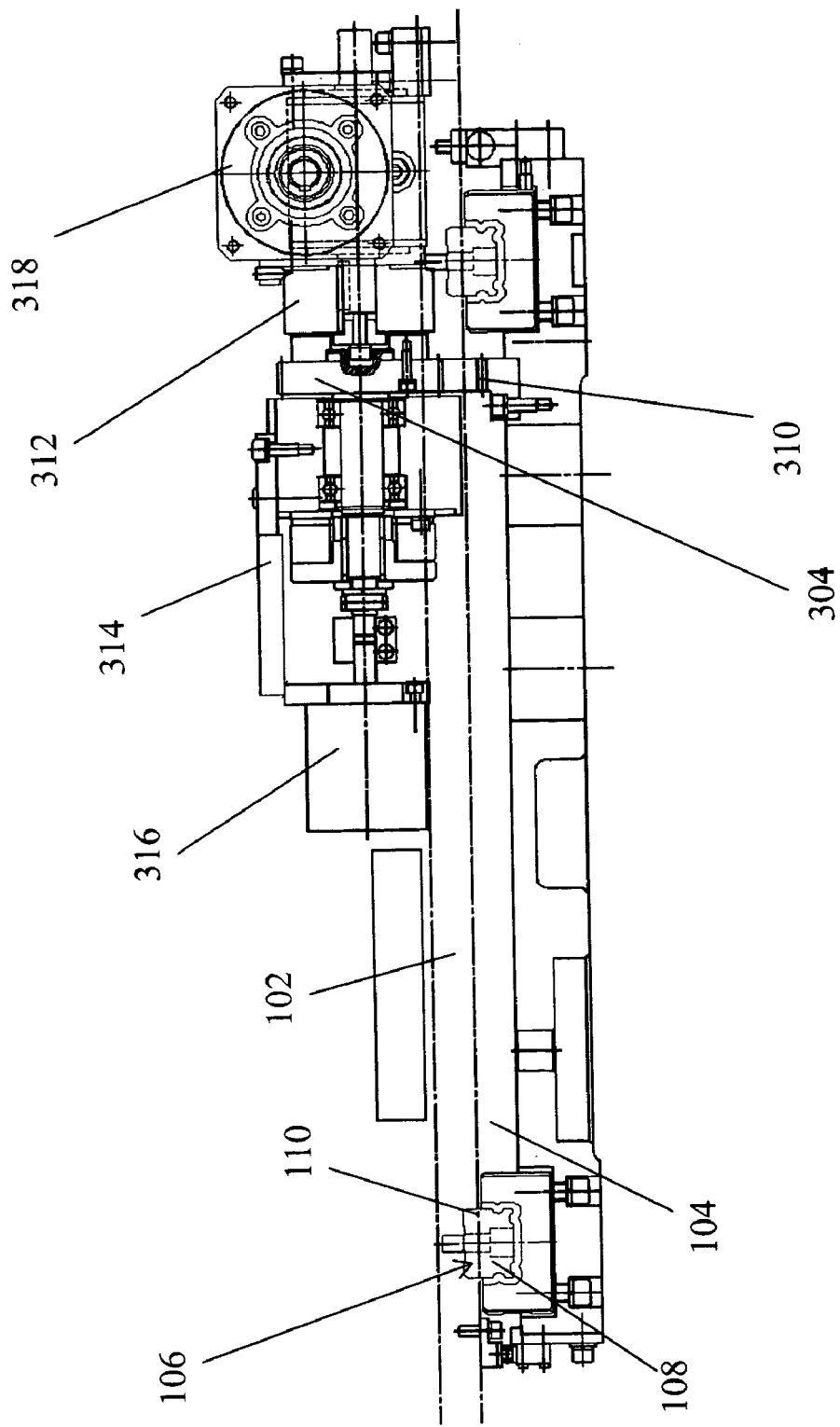
FIG. 3 shows the front cross-section view of the drive for lateral movement of the patient support table according to one embodiment of the present invention.
Figure 4:
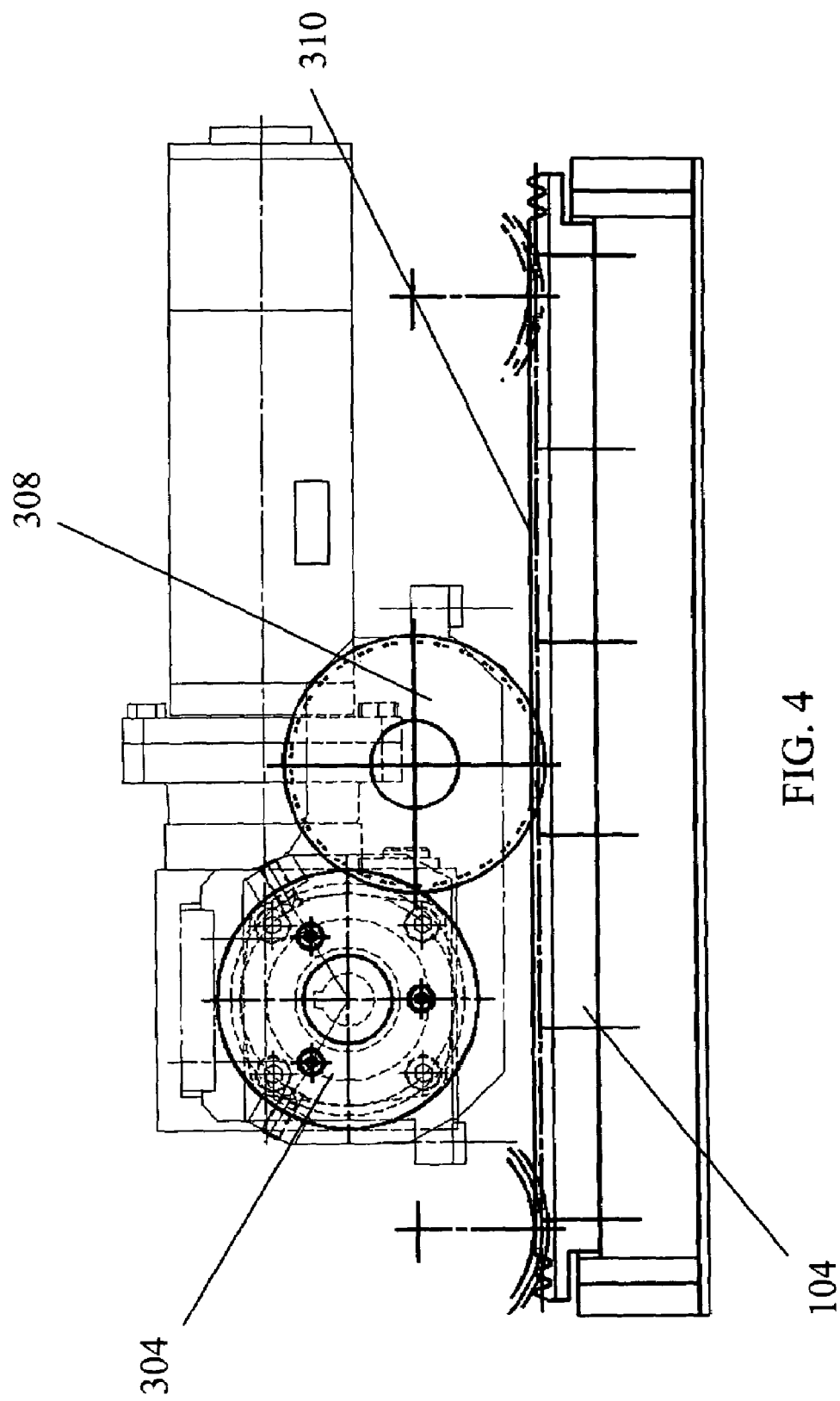
FIG. 4 shows the X—X view of the drive means of FIG. 3.

FIG. 2 to 4 show perspective, front and side views of a drive system including the second drive 302 according to one embodiment of this invention. Accordingly, the second drive 302 comprises a drive motor 318 (driving member) coupled to a drive gear 304 through a transmission e.g. a gear box 311 and a clutch 312. The drive gear 304 drives a pinion 308, wherein the drive motor 318, the drive gear 304 and the pinion 308 are mounted on the longitudinal plate 102 (mounting member). A rack 310 (driven member) is mounted on the tilt plate 104 (see FIG. 3 and FIG. 4) such that the pinion 308 engages with the rack 310 for transmitting the drive from the drive motor 318 to the patient support surface for effecting lateral movement of the patient support surface.

In this configuration, the drive motor 318 (driving member) moves along with the patient support surface and the rack 310 (driven member) is configured fixed on the tilt plate 104.

It should be noted that the configuration of the second drive 302 according to this invention increases the compactness of the drive system, enables mounting on to the longitudinal plate 102 (mounting member) in combination with the first drive 202 and also provides a smooth lateral motion to the patient support table, without any shock or jerk to the patient. Furthermore, servicing of the table becomes significantly easy, as the first drive 202 and the second drive 302 are accessible from above the longitudinal plate 102, thereby eliminating the need for removing the table covers for servicing.

In other embodiments, an optional mechanism e.g. a user operable lever in combination with a clutch 312, for facilitating manual lateral movement to the patient support surface, may be provided in combination with the second drive 302. This would provide increased convenience to the user for positioning a patient within the imaging area.

It should also be noted that the drive gear 304 and pinion 308 are configured to provide a drive stroke from the center of the patient support surface, for increased convenience in patient positioning. This can be achieved by arranging the drive gear 304 and the pinion 308 well within the edges of the longitudinal plate, i.e., without any projections beyond the longitudinal edges of the longitudinal plate 102.

However, in other embodiments, the drive gear 304 may be configured to directly engage the rack 310. This arrangement may be implemented in connection with drive systems in which speed change by pinion 308 is not possible due to space constraint or not required, without compromising the stroke distribution.

For example, the drive motor 318 may be a brushless DC motor and the clutch 312 may be an electromagnetic clutch.

In further examples, the gear arrangement may include a non-reversible gearbox comprising a plurality of worm gears for providing predetermined torque and speed to the patient support surface. It should be noted that the use of worm gear box 311 provides for a better drive orientation and increased compactness to the second drive 302.

In an embodiment, a brake mechanism such as, for example, a fail-safe electromagnetic brake 314 may be connected in combination with the second drive 302 as shown in FIG. 2.

It should be noted that the use of a fail-safe electromagnetic brake configured with a positive lock would hold the table rigidly during patient loading and unloading, and hence increase the safety by preventing slippage during positioning patients over the table.

In yet another embodiment, a feedback device 316 such as, for example, an encoder pulse monitoring unit comprising a motor side incremental encoder or a load side absolute encoder is connected to the second drive as shown in FIG. 2 for providing feedback to the brake 314 such that the brake 314 is operated to stop table movement in case of any malfunctioning such as power failure, cable detachments etc.

Thus, various embodiments of this invention provide a table drive system for a medical imaging apparatus. Further embodiments of this invention provide a patient support table comprising a drive system configured to provide a compact structure, smooth drive, easy access and increased safety to patients.

While the invention has been described in terms of various specific embodiments, those skilled in the art will recognize that the invention can be practiced with modifications such as, for example, first drive integrally coupled to second drive, simultaneously operable first and second drives, etc. The second drive may be modified to include one of a hydraulic actuator, a pneumatic actuator or a friction drive, with driving member mounted on to longitudinal plate and driven member mounted to tilt plate. However, all such modifications are deemed to have been covered within the scope of the claims appended hereto.

We claim:

1. A table drive system for a medical imaging apparatus comprising:
   at least one first drive for moving a patient support surface in at least one first direction; and
   at least one second drive for moving the patient support surface in at least one second direction,
   wherein the at least one first drive and the at least one second drive are mounted on a common mounting member, and
   wherein the second drive further comprises a rack and pinion arrangement.

2. The table drive system according to claim 1 wherein the first direction further comprises a longitudinal direction and the second drive direction farther comprises a lateral direction.

3. The table drive system according to claim 1 wherein the first drive further comprises at least one of a friction drive, a hydraulic actuator and a pneumatic actuator.

4. The table drive system according to claim 1 wherein the second drive is configured to provide a drive stroke from a center of the patient support surface.

5. The table drive system according to claim 1 further comprising a transmission, wherein the transmission includes a plurality of worm gears in combination with the second drive, the transmission being operably coupled to the patient support surface and operably coupled to the at least one first drive.

6. The table drive system according to claim 5 further comprising a fail brake mechanism in combination with the second drive.

7. The table drive system according to claim 6 further comprising a brake mechanism operated in response to the output from a feed back device.

8. The table drive system according to claim 1 wherein the mounting member further comprises a longitudinal plate coupled to the patient support surface.

9. A drive system for a patient support table comprising:
   at least one driven member for moving a patient support surface;
   at least one driving member in coordinating relationship with the at least one driven member, wherein the at least one driving member is configured to move along with the patient support surface; and
   a fail safe electromagnetic brake in combination with the at least one driving member.

10. The drive system according to claim 9 wherein the driving member is mounted on a longitudinal plate of the patient support table.

11. The drive system according to claim 9 wherein the driven member further comprises at least one rack mounted in fixed position.

12. The table drive system according to claim 9 further comprising a transmission, wherein the transmission further comprises;
   at least one of an electro magnetic clutch; and
   a plurality of worm gears in combination with the driving member.

13. The table drive system according to claim 9 wherein the second drive is configured to provide a drive stroke from a center of the patient support surface.

14. A patient support table comprising:
   a patient support surface;
   a mounting member coupled to the patient support surface, said mounting member configured to support a first drive adapted for moving the patient support surface in at least one first direction, and a second drive adapted for moving the patient support surface in at least one second direction, and said second drive comprising at least one driving member configured to move along with the patient support surface,
   wherein a driven member includes a rack disposed in fixed position relative to the driving member.

15. The patient support table according to claim 14 wherein the mounting member further comprises a longitudinal plate coupled to the patient support surface.

16. The patient support table according to claim 14 wherein the first drive is adapted for moving the patient support surface along a longitudinal direction.

17. The patient support table according to claim 14 wherein the second drive is adapted for moving the patient support surface along a lateral direction.

18. The patient support table according to claim 17 wherein the second drive is configured to provide a drive stroke from a center of the patient support surface.

19. The patient support table according to claim 14 wherein the driving member is mounted on a longitudinal plate.

20. The patient support table according to claim 14 wherein the patient support table is operably coupled to a magnetic resonance imaging device.

* * * * *